(12) United States Patent
Sasaki et al.

(10) Patent No.: US 12,026,872 B2
(45) Date of Patent: Jul. 2, 2024

(54) DIAGNOSIS ASSISTING SYSTEM, DIAGNOSIS ASSISTING METHOD AND DIAGNOSIS ASSISTING PROGRAM

(71) Applicant: SUMITOMO CHEMICAL COMPANY, LIMITED, Tokyo (JP)

(72) Inventors: Katsunori Sasaki, Tokyo (JP); Tomoyuki Watanabe, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 485 days.

(21) Appl. No.: 17/054,143

(22) PCT Filed: May 29, 2019

(86) PCT No.: PCT/JP2019/021386
§ 371 (c)(1),
(2) Date: Nov. 9, 2020

(87) PCT Pub. No.: WO2019/235335
PCT Pub. Date: Dec. 12, 2019

(65) Prior Publication Data
US 2021/0125332 A1    Apr. 29, 2021

(30) Foreign Application Priority Data

Jun. 5, 2018 (JP) ................................. 2018-107579

(51) Int. Cl.
*G06T 7/00* (2017.01)
*G06N 3/04* (2023.01)
(Continued)

(52) U.S. Cl.
CPC ............. *G06T 7/0012* (2013.01); *G06N 3/04* (2013.01); *G16H 30/40* (2018.01); *G16H 50/20* (2018.01);
(Continued)

(58) Field of Classification Search
CPC ......... G06T 7/0012; G06T 2207/20081; G06T 2207/20084; G16H 50/20; G16H 30/40;
(Continued)

(56) References Cited

U.S. PATENT DOCUMENTS

2014/0101080 A1    4/2014  Lee et al.
2016/0171682 A1*   6/2016  Abedini ................. G16H 30/20
                                                382/132
(Continued)

FOREIGN PATENT DOCUMENTS

CN         105975793 A      9/2016
JP         2014-135066 A    7/2014
(Continued)

OTHER PUBLICATIONS

Bejnordi, Babak Ehteshami, et al. "Diagnostic assessment of deep learning algorithms for detection of lymph node metastases in women with breast cancer." Jama 318.22 (2017): 2199-2210. (Year: 2017).*

(Continued)

*Primary Examiner* — Amandeep Saini
*Assistant Examiner* — Denise G Alfonso
(74) *Attorney, Agent, or Firm* — Foley & Lardner LLP

(57) ABSTRACT

A diagnosis assisting system, a diagnosis assisting method, and a diagnosis assisting program provide information that contributes to an objective diagnosis, with a server of a diagnosis assisting system including a learned model acquisition unit that acquires a plurality of learned models, each of which is generated by machine learning, inputs information based on an image obtained by imaging a diagnostic target, and outputs information that indicates a diagnosis result of the diagnostic target; an image acquisition unit that acquires an image to be analyzed; a calculation unit that performs calculation based on the plurality of learned mod- (Continued)

els acquired on the image acquired, and calculates one piece of information about a diagnosis using the plurality of learned models; and an output unit that outputs the information calculated by the calculation unit.

10 Claims, 3 Drawing Sheets

(51) Int. Cl.
*G16H 30/40* (2018.01)
*G16H 50/20* (2018.01)
*A61B 5/055* (2006.01)
*A61B 5/346* (2021.01)
*A61B 6/00* (2006.01)
*A61B 6/03* (2006.01)

(52) U.S. Cl.
CPC ............... *A61B 5/055* (2013.01); *A61B 5/346* (2021.01); *A61B 6/032* (2013.01); *A61B 6/5217* (2013.01); *G06T 2207/20081* (2013.01); *G06T 2207/20084* (2013.01)

(58) Field of Classification Search
CPC ............ G16H 70/60; G06N 3/04; G06N 3/08; G06N 20/00; A61B 5/346; A61B 5/055; A61B 6/032; A61B 6/5217
See application file for complete search history.

(56) References Cited

U.S. PATENT DOCUMENTS

| | | | |
|---|---|---|---|
| 2017/0262561 A1* | 9/2017 | Yoshida | G06F 11/3447 |
| 2018/0276821 A1* | 9/2018 | Lin | A61B 8/5223 |
| 2019/0042959 A1* | 2/2019 | Kawagishi | G16H 50/20 |
| 2019/0110754 A1* | 4/2019 | Rao | G06N 7/00 |
| 2020/0085290 A1* | 3/2020 | Wang | A61B 3/12 |
| 2020/0272864 A1* | 8/2020 | Faust | G06V 10/764 |
| 2022/0230750 A1* | 7/2022 | Rim | A61B 5/7267 |

FOREIGN PATENT DOCUMENTS

| | | |
|---|---|---|
| JP | 2017-153691 A | 9/2017 |
| KR | 10-2014-0042531 A | 4/2014 |
| WO | WO-2016/152242 A1 | 9/2016 |

OTHER PUBLICATIONS

International Searching Authority, "International Search Report," issued in connection with International Patent Application No. PCT/JP2019/021386, dated Aug. 27, 2019.
International Searching Authority, "Written Opinion," issued in connection with International Patent Application No. PCT/JP2019/021386, dated Aug. 27, 2019.
Office Action issued in corresponding Japanese Patent Application No. 2020-523660, dated Apr. 6, 2023.
Office Action issued in corresponding Chinese Patent Application No. 201980036934.1 dated Dec. 18, 2023 (20 pages).
Office Action issued in corresponding Korean Patent Application No. 10-2020-7034672 dated Feb. 19, 2024 (5 pages).

* cited by examiner

【Figure1】
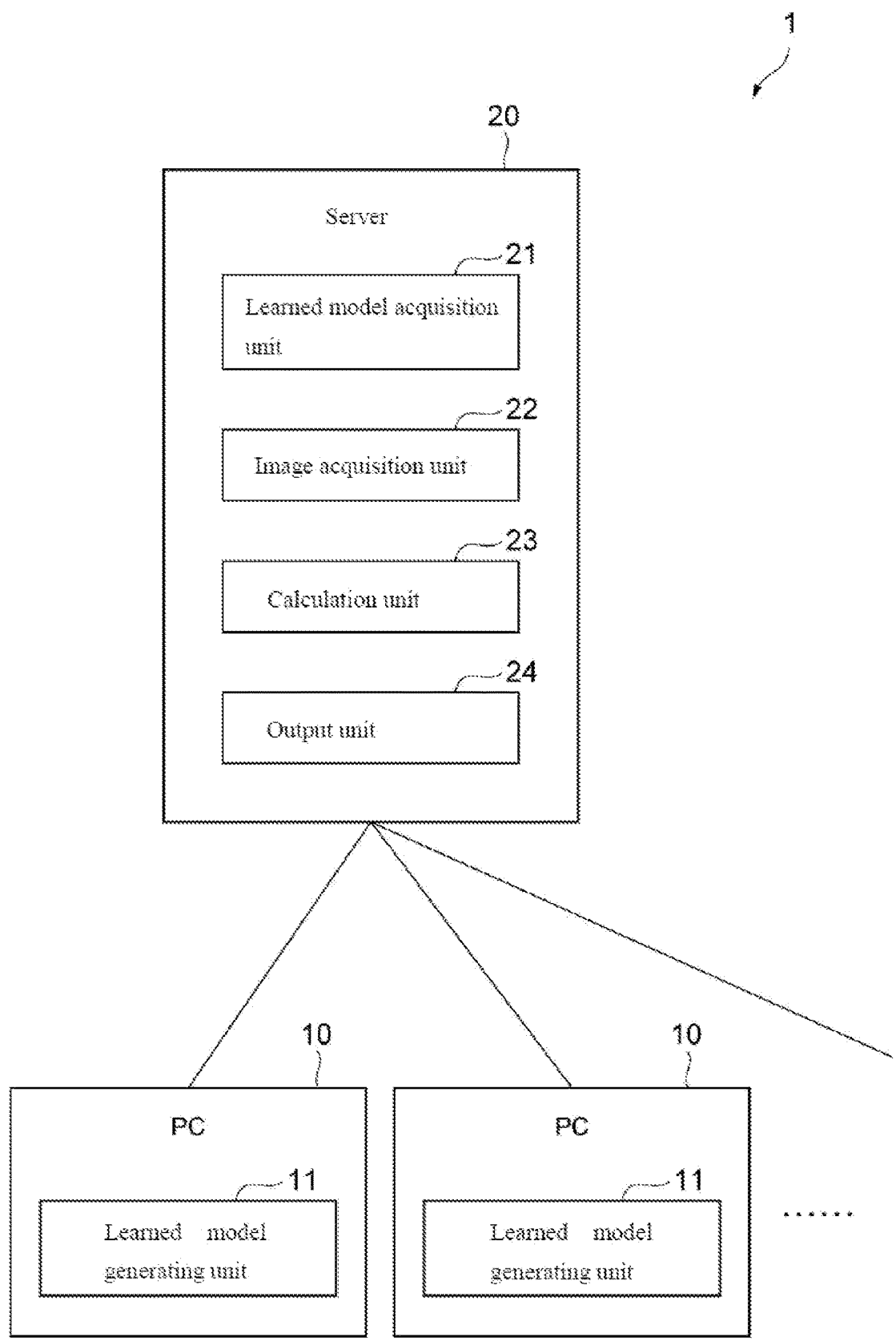

[Figure2]
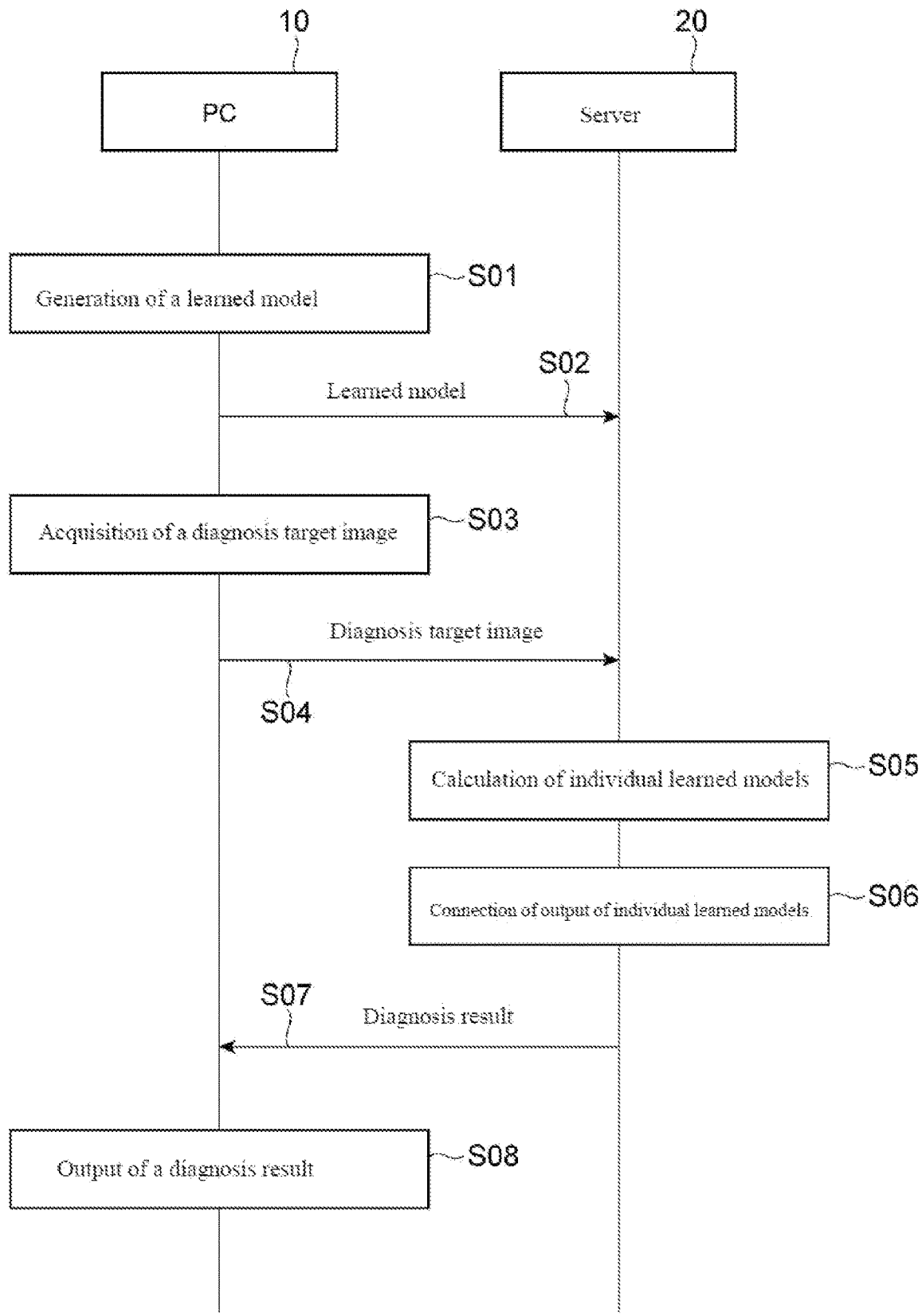

【Figure3】
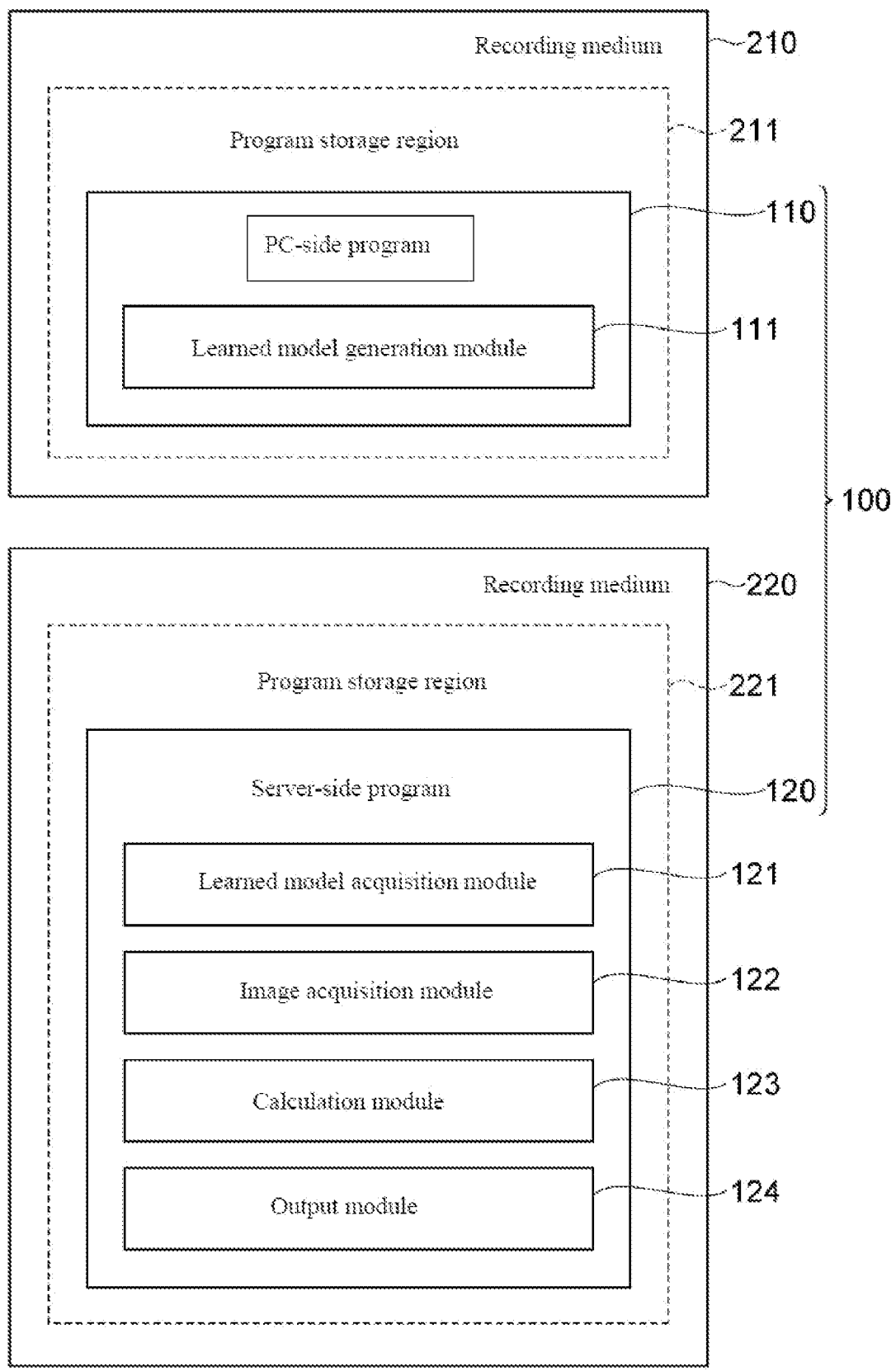

DIAGNOSIS ASSISTING SYSTEM, DIAGNOSIS ASSISTING METHOD AND DIAGNOSIS ASSISTING PROGRAM

RELATED APPLICATIONS

The present application claims priority under 37 U.S.C. § 371 to International Patent Application No. PCT/JP2019/021386, filed May 29, 2019, which claims priority to and the benefit of Japanese Patent Application No. 2018-107579, filed on Jun. 5, 2018. The contents of these applications are hereby incorporated by reference in their entireties.

TECHNICAL FIELD

The present invention relates to a diagnosis assisting system, a diagnosis assisting method, and a diagnosis assisting program that pertain to diagnosis based on an image.

BACKGROUND ART

In the past, expert pathologists have observed pathological specimens on a glass slides under a microscope in the field of pathological tissue examination (pathological diagnosis) and thereby performed diagnosis. This diagnosis has been subjective determination that has been largely dependent on personal experience and knowledge of the observing pathologist. For this reason, it has been difficult to make an objective diagnosis. Thus, in the field of pathological diagnosis, a peer review system in which other pathologists has evaluated and reviewed diagnosis results of a certain pathologist, and thereby a risk of subjective determination has been reduced has been adopted. However, it has been extremely inefficient to perform peer review on all pathological diagnosis results. In addition, since final determination in the peer review has also been conducted by discussion between the pathologists, this has resulted in depending greatly on personal experience, knowledge, and the influential voice of a person in charge. Therefore, subjective elements have been unable to be excluded in principle, and it has been difficult to objectively make a pathological diagnosis.

Meanwhile, attempts have been made to automate pathological diagnosis based on an image using machine learning (for example, Patent Literature 1).

Citation List

Patent Literature

Patent Literature 1: PCT International Publication No. WO2016/152242

SUMMARY OF INVENTION

Problem to be Solved by the Invention

The pathological diagnosis using the machine learning contributes to a more efficient pathological diagnosis. However, to make an objective pathological diagnosis, there is a need to collect large-scale learning data (teacher data) for performing the machine learning on which a consensus is obtained. In collecting the learning data, interpersonal discussion between the pathologists about each case is essential, and the aforementioned problem occurs. That is, the exclusion of the subjective elements is not easy only by using merely the machine learning, and collecting the large-scale learning data on which a consensus is obtained is also unrealistic.

The present invention was made in view of the above circumstances, and an object thereof is to provide a diagnosis assisting system, a diagnosis assisting method, and a diagnosis assisting program capable of providing information that contributes to an objective diagnosis.

Means for Solving the Problem

A diagnosis assisting system according to the present invention includes: learned model acquisition means configured to acquire a plurality of learned models that are generated by machine learning, input information based on an image obtained by imaging a diagnostic target, and output information that indicates a diagnosis result of the diagnostic target; image acquisition means configured to acquire an image to be analyzed; calculation means configured to perform calculation based on the plurality of learned models acquired by the learned model acquisition means on the image acquired by the image acquisition means, and calculate one piece of information about a diagnosis using the plurality of learned models; and output means configured to output the information calculated by the calculation means.

In the diagnosis assisting system according to the present invention, calculation is performed on an image based on a plurality of learned models that are individually generated, and one piece of information about a diagnosis is calculated. The calculated one piece of information about a diagnosis is, for instance, information that indicates a diagnosis result itself of the image, or information that indicates distribution of the diagnosis results among the plurality of learned models. Even if the individual learned model is not sufficiently objective, the one piece of information about the diagnosis is calculated using the plurality of learned models in this way, and thereby the calculated information can be made to contribute to the objective diagnosis. That is, according to the diagnosis assisting system of the present invention, the information that contributes to the objective diagnosis can be provided.

The calculation means may be configured to input information based on the image acquired by the image acquisition means to each of the plurality of learned models acquired by the learned model acquisition means, and calculate one piece of information about a diagnosis from information that indicates a diagnosis result output from each of the plurality of learned models. According to this constitution, the one piece of information about the diagnosis can be calculated using the plurality of learned models in an adequate and reliable manner. As a result, the information that contributes to the objective diagnosis can be reliably and adequately provided.

The diagnosis assisting system may further include learned model generation means configured to acquire the image obtained by imaging the diagnostic target and the information that indicates the diagnosis result of the diagnostic target, both of which are learning data used for the machine learning, perform the machine learning using information based on the image that is the acquired learning data as an input value and using the information that indicates the diagnosis result and is the acquired learning data as an output value, and generate a learned model. The learned model acquisition means may be configured to acquire the learned model generated by the learned model generation means. According to this constitution, the individual learned models can be generated, and the present invention can be carried out in an adequate and reliable manner.

The learned model acquisition means may be configured to acquire the plurality of learned models including a neural network. According to this constitution, the learned models can be made adequate, and the present invention can be carried out in an adequate and reliable manner.

Meanwhile, in addition to the constitution in which the present invention can be described as the invention of the diagnosis assisting system as described above, the present invention can also be described as inventions of a diagnosis assisting method and a diagnosis assisting program as follows. These are merely different in category, and are substantially the same inventions that produce similar operation and effects.

That is, a diagnosis assisting method according to the present invention is a method for operating a diagnosis assisting system, and includes: a learned model acquiring step of acquiring a plurality of learned models that are generated by machine learning, input information based on an image obtained by imaging a diagnostic target, and output information that indicates a diagnosis result of the diagnostic target; an image acquiring step of acquiring an image to be analyzed; a calculating step of performing calculation based on the plurality of learned models acquired in the learned model acquisition step on the image acquired in the image acquisition step, and calculating one piece of information about a diagnosis using the plurality of learned models; and an outputting step of outputting the information calculated in the calculating step.

A diagnosis assisting program according to the present invention causes a computer to function as: learned model acquisition means configured to acquire a plurality of learned models that are generated by machine learning, input information based on an image obtained by imaging a diagnostic target, and output information that indicates a diagnosis result of the diagnostic target; image acquisition means configured to acquire an image to be analyzed; calculation means configured to perform calculation based on the plurality of learned models acquired by the learned model acquisition means on the image acquired by the image acquisition means, and calculate one piece of information about a diagnosis using the plurality of learned models; and output means configured to output the information calculated by the calculation means.

Effects of the Invention

According to the present invention, even if the individual learned model is not sufficiently objective, one piece of information about a diagnosis is calculated using a plurality of learned models, and thereby the calculated information can be made to contribute to an objective diagnosis. That is, according to the present invention, the information that contributes to the objective diagnosis can be provided.

BRIEF DESCRIPTION OF THE DRAWINGS

FIG. 1 is a diagram illustrating a constitution of a diagnosis assisting system according to an embodiment of the present invention.

FIG. 2 is a sequence diagram illustrating a process (a diagnosis assisting method) performed by the diagnosis assisting system according to the embodiment of the present invention.

FIG. 3 is a diagram illustrating an architecture of a diagnosis assisting program according to an embodiment of the present invention along with a recording medium.

EMBODIMENTS OF THE INVENTION

Hereinafter, embodiments of a diagnosis assisting system, a diagnosis assisting method, and a diagnosis assisting program according to the present invention will be described along with the drawings. In the description of the drawings, the same elements are given the same reference signs, and duplicate description thereof will be omitted.

FIG. 1 illustrates a diagnosis assisting system 1 according to the present embodiment. The diagnosis assisting system 1 is a system (digital pathology system) that assists with a diagnosis based on an image. A diagnosis to be assisted with is a pathological diagnosis, that is, a diagnosis of, for instance, presence/absence of a lesion based on an image of a pathological specimen that includes pathological tissue collected from a human body or the like. The way that the diagnosis assisting system 1 assists with a diagnosis will be described below.

As illustrated in FIG. 1, the diagnosis assisting system 1 is configured to include a plurality of personal computers (PCs) 10 and a server 20. The diagnosis assisting system 1 according to the present embodiment assists with the diagnosis using learned models generated by machine learning.

The PC 10 is a device that generates a learned model by machine learning. The PC 10 is used by a user such as a medical pathologist, a pathologist, etc. who makes a diagnosis. The PC 10 constitutes a personal system of the user. As illustrated in FIG. 1, the PC 10 is provided for each of a plurality of users. The PCs 10 and the server 20 are connected through_a wired or wireless network such as the Internet or a telephone network, and can mutually transmit and receive information.

The server 20 is a device that acquires the plurality of learned models generated by the plurality of PCs 10 and performs information processing about the assistance with the diagnosis. The server 20 is provided by an administrator of the diagnosis assisting system 1. The server 20 may be made up of a cloud system.

The PCs 10 and the server 20 are each made up of a computer that includes hardware such as a central processing unit (CPU), a graphics processing unit (GPU), a memory, a communication module, and a storage device that is a hard disk drive (HDD) or a solid state drive (SDD). These components of the PCs 10 and the server 20 are operated by a program or the like, and thereby functions (to be described below) of the PCs 10 and the server 20 are exhibited. The PCs 10 and the server 20 may be a computer system made up of a plurality of computers.

As illustrated in FIG. 1, the PC 10 is configured to include a learned model generating unit 11 as a function according to the present embodiment. The PC 10 may include a function which a typical PC has in addition to the above functions.

The learned model generating unit 11 is learned model generation means that acquires learning data used in machine learning and performs the machine learning using the acquired learning data to generate a learned model. The learning data includes an image obtained by imaging a diagnostic target, and diagnostic information that is information indicating a diagnostic result of the diagnostic target. The image obtained by imaging the diagnostic target is a pathological tissue image that is an image of the pathological specimen that includes the pathological tissue collected from the human body or the like. The image is obtained, for instance, by imaging by a camera connected to a microscope. For example, a user interface provided in the PC 10 is operated by a user, and the learned model generating unit 11 acquires the image obtained as described above as the learning data. The PC 10 may be connected to an automatic imaging device such as a virtual slide scanner, and the learned model generating unit 11 may acquire numerous images that are continuously picked up by the automatic imaging device. The images correspond to input of the learned model.

To appropriately perform the machine learning, the learned model generating unit 11 may also unify, i.e. normalize, sizes of the acquired images (e.g., the number of longitudinal and transverse pixels of the images) into a preset size. The normalization of the images is performed, for instance, by scaling down, scaling up, trimming, etc. the images. The learned model generating unit 11 may also perform various types of processing, such as adjustment of a contrast, a change in color, and a change in format, on the acquired images.

The image used as the learning data is subjected to pathological diagnosis in advance by a user of the PC 10 or the like. That is, presence/absence of a lesion of a predetermined type (a diagnosis type) is diagnosed with respect to the image. The diagnostic information serving as the learning data is, for instance, information that is based on the diagnosis and indicates presence/absence of a lesion of a preset type. To be specific, the diagnostic information is binary value information of 0 or 1, 1 indicating that there is a lesion (an abnormal state) and 0 indicating that there is no lesion (a normal state). The diagnostic information serving as the learning data may be information that indicates presence/absence of a lesion with respect to a plurality of types of lesions. In this case, the diagnostic information is, for instance, a vector, and the number of the dimensions of the vector is the number of lesions of a plurality of preset types. An element of a type in which there is a lesion in the vector is set to be 1, and an element of a type in which there is no lesion is set to be 0. The diagnostic information that is this vector can be generated based on a name of the diagnosis that is freely mentioned by a user or the like. The diagnostic information corresponds to output of the learned model. A user interface provided in the PC 10 is operated by a user, and the learned model generating unit 11 acquires the diagnostic information as the learning data. The acquired diagnostic information is associated with an image of a diagnosis source. Much learning data is typically prepared to perform the machine learning.

The learned model generated by the learned model generating unit 11 is a model that inputs the information based on the image and outputs information that indicates the diagnosis result, i.e. predicts the diagnosis result. For example, the learned model outputs information that indicates presence/absence of a lesion for an image. The learned model includes a neural network. The learned model may include a convolutional neural network. Furthermore, the learned model may include a neural network having a plurality of layers (e.g., eight or more layers). That is, the learned model may be generated by deep learning.

For example, the neural network inputs a pixel value of each pixel of an image, and outputs the information that indicates the presence/absence of the lesion. An input layer of the neural network is provided with neurons having the same number as pixels of the image. The output layer of the neural network is provided with a neuron for outputting the information that indicates the presence/absence of the lesion. For example, if a lesion of a diagnostic target is a specific single lesion, an output layer is provided with one neuron corresponding to the single lesion. If the diagnostic target is a plurality of types of lesions (if the diagnostic information is the aforementioned vector), the output layer is provided with a plurality of neurons corresponding to the plurality of types of lesions. An output value of the neuron is a value corresponding to the diagnostic information of the learning data, for instance a value between 0 and 1. In this case, as the value of the neuron becomes larger (as the value becomes close to 1), it indicates that there is a lesion (abnormality). As the value of the neuron becomes smaller (as the value becomes close to 0), it indicates that there is no lesion (normality).

The learned model generating unit 11 performs the machine learning to generate the neural network by setting each pixel value of the acquired image as an input value to the neural network and simultaneously setting the diagnostic information corresponding to the acquired image as an output value of the neural network. When setting the pixel values as the input values, the pixel values are set as input values of the neurons associated with the respective pixels (positions of the pixels in the image). The machine learning itself can be performed in the same way as a conventional machine learning algorithm.

In the above example, the input value to the neural network is set as the pixel value of the image. However, in place of the pixel value or in addition to the pixel value, the input value may be set as a characteristic amount extracted from the image. The extraction of the characteristic amount from the image can be performed by a conventional arbitrary method. When the neural network is generated, outlier data may be eliminated as noise by performing statistical processing on the learning data. The elimination of the noise can be performed in the same way as a conventional method.

The learned model generating unit 11 transmits the generated learned model to the server 20. The generation of the learned model and the transmission of the learned model to the server 20 are performed at each PC 10. The learned model generated at each PC 10 is used, and a diagnosis may be made of an unknown image at each PC 10. As will be described below, the PC 10 may transmit and receive an image and information about a diagnosis to and from the server 20. The above is the function of the PC 10 according to the present embodiment.

As illustrated in FIG. 1, the server 20 is configured to include a learned model acquisition unit 21, an image acquisition unit 22, a calculation unit 23, and an output unit 24 as functions according to the present embodiment.

The learned model acquisition unit 21 is learned model acquisition means that acquires a plurality of learned models. The learned model acquisition unit 21 receives and acquires the learned model that is generated and transmitted at each PC 10. The plurality of learned models acquired by the learned model acquisition unit 21 are stored (accumulated) in the server 20, and are used for calculation by the calculation unit 23. The plurality of learned models acquired may be associated with PC 10 that generated the learned model and be stored.

The image acquisition unit 22 is image acquisition means that acquires an image to be analyzed. The image to be analyzed is a pathological tissue image targeted for analysis using the plurality of learned models. For example, the image is acquired in the same way as the image of the learning data at the PC 10, and is transmitted to the server 20. The image acquisition unit 22 receives and acquires the image. The image acquisition unit 22 may perform image processing such as normalization of the image on the image in the same way as the image of the learning data. The image processing may be performed at the PC 10. The image may be acquired by a method other than the above method. The image acquisition unit 22 outputs the acquired image to the calculation unit 23.

The calculation unit 23 is calculation means that performs calculation based on the plurality of learned models acquired by the learned model acquisition unit 21 on the image acquired by the image acquisition unit 22 and calculates one piece of information related to the diagnosis caused by the plurality of learned models. The calculation unit 23 inputs the information based on the image to each of the plurality of learned models, and calculates one piece of information about the diagnosis from the information that indicates the diagnosis result output from each of the plurality of learned models.

As described above, the learned model generated at the PC 10 is generated based on a previous pathological diagnosis from, for instance, a user of the PC 10. Accordingly, the generated learned model is made to reproduce a conventional diagnostic criterion (logic of thought) of, for instance, a user of the PC 10 who has performed pathological diagnosis with high accuracy. That is, when the previous pathological diagnosis is not objective, the generated learned model cannot be assumed to be objective either. In the present embodiment, even if the individual learned model is not sufficiently objective, one piece of information about the diagnosis is calculated using the plurality of learned models, and thereby the calculated information is made to contribute to an objective diagnosis.

To be specific, the calculation unit 23 calculates one piece of information about the diagnosis using the plurality of learned models as follows. The calculation unit 23 inputs the image to be analyzed from the image acquisition unit 22, and simultaneously reads out the plurality of learned models that are acquired by the learned model acquisition unit 21 and are stored in the PCs 10. For example, the calculation unit 23 calculates one diagnosis result of the image to be analyzed as one piece of information using the plurality of learned models, i.e., predicts the diagnosis result. In this case, the calculation unit 23 performs calculation corresponding to each neural network using a pixel value of each pixel of the image to be analyzed as an input value to each neural network that is a learned model, and obtains an output value from each neural network. The calculation unit 23 performs connection based on these output values, and calculates one diagnosis result.

For example, the calculation unit 23 calculates one diagnosis result from each output value. The calculation unit 23 compares each output value with a preset threshold, and determines that there is a lesion when the output value is more than or equal to the threshold and that there is no lesion when the output value is less than the threshold. Since there are only as many output values as the number of the plurality of learned models, the number of performed determinations corresponds to the number of the plurality of learned models. When there are output values corresponding to a plurality of types of lesions, the calculation unit 23 performs the determination on each type of lesion. The calculation unit 23 compares the number of output values indicating a determination that there is a lesion with the number of output values indicating a determination that there is no lesion.

When the number of determinations that there is a lesion is larger, the calculation unit 23 determines that there is a lesion as one diagnosis result of the image to be analyzed using the plurality of learned models. When the number of determinations that there is no lesion is larger, the calculation unit 23 determines that there is no lesion as one diagnosis result of the image to be analyzed using the plurality of learned models. This is an example of information that indicates one diagnosis result. Alternatively, the calculation unit 23 may use distribution of the output values from each neural network, i.e., distribution of the diagnosis results of the individual learned models, as the information that indicates one diagnosis result.

In place of or in addition to the foregoing, the calculation unit 23 may calculate information other than a direct diagnosis result as one piece of information about the diagnosis using the plurality of learned models. For example, the calculation unit 23 may calculate information that indicates consistency/inconsistency between the diagnosis result according to the learned model associated with the PC 10 that is a generation source of the image to be analyzed and the diagnosis result according to another learned model. To be specific, the calculation unit 23 may calculate the number of consistencies between the diagnosis results and the number of inconsistencies between the diagnosis results. That is, the calculation unit 23 may analyze a difference between the diagnosis results using the learned models. Based on this information, a user can check how consistent the user's diagnosis results are with those of another user. That is, the user can carry out peer review.

The calculation unit 23 may calculate one piece of information about the diagnosis according to a method other than the above method. For example, the calculation unit 23 may perform digital processing such as conventional arbitrary statistical processing on information output from the individual learned model, and calculate one piece of information about the diagnosis. The calculation unit 23 outputs one piece of information about the diagnosis using the plurality of learned models that have been calculated to the output unit 24.

The output unit 24 is output means that outputs the information calculated by the calculation unit 23. The output unit 24 inputs the information from the calculation unit 23. For example, the output unit 24 transmits and outputs information to the PC 10 that is a transmission source of an analysis image. The information is received by and displayed on the PC 10. Thereby, a user of the PC 10 can use of the diagnosis with reference to one piece of information about the diagnosis using the plurality of learned models. The output unit 24 may output information through a method other than the above method. These are the functions of the server 20 according to the present embodiment.

Next, a diagnosis assisting method that is a process performed by the diagnosis assisting system 1 according to the present embodiment (an operation method which the diagnosis assisting system 1 performs) will be described using a sequence diagram of FIG. 2. First, the learned model generating unit 11 at each of the PCs 10 which are included in the diagnosis assisting system 1 acquires learning data, uses the acquired learning data, performs machine learning, and generates a learned model (a learned model generating step S01). The generated learned model is transmitted from the learned model generating unit 11 to the server 20 (S02).

In the server 20, the learned models transmitted from the plurality of PCs 10 are received and acquired by the learned model acquisition unit 21 (a learned model acquiring step S02). The plurality of learned models that have been acquired are stored in the server 20.

Then, an image to be analyzed is acquired by the PC 10 (S03). The image to be analyzed is a pathological tissue image that is imaged by, for instance, a camera connected to a microscope. The image to be analyzed is transmitted from the PC 10 to the server 20 (S04). In the server 20, the image to be analyzed transmitted from the PC 10 is received and acquired by the image acquisition unit 22 (an image acquiring step S04).

Then, the calculation unit 23 inputs information based on the image to each of the plurality of learned models, performs calculation corresponding to each of the plurality of learned models, and acquires information that indicates a diagnosis result output from each of the plurality of learned models (a calculating step S05). Then, the calculation unit 23 performs connection of the information that indicates the diagnosis result output from each of the plurality of learned models, and calculates one piece of information about a diagnosis, for instance one diagnosis result, using the plurality of learned models (a calculating step S06).

Then, the information calculated by the calculation unit 23, for instance, the information that indicates one diagnosis result, is transmitted and output from the output unit 24 to the PC 10 (an outputting step S07). The information is received by the PC 10, and output such as display of the information is performed (S08). The foregoing is the diagnosis assisting method according to the present embodiment.

As described above, in the present embodiment, the calculation is performed on the image to be analyzed based on the plurality of learned models that are generated individually, and one piece of information about the diagnosis is calculated. Even if the individual learned model is not sufficiently objective, one piece of information about the diagnosis is calculated using the plurality of learned models in this way, and thereby the calculated information can be made to contribute to the objective diagnosis from which the subjective element is eliminated. That is, according to the present embodiment, information that contributes to the objective diagnosis can be provided.

As described above, the learned model indicates the conventional diagnostic criterion of, for instance, the user of the PC 10. One piece of information about the diagnosis is calculated based on the plurality of learned models, and thereby the diagnostic criterion can be standardized. If the individual learned model is generated by the learning data of the user of the world, global standardization of the diagnostic criterion can be attempted.

Since the information about the diagnosis is calculated by information processing based on the image, the diagnosis can be made efficient, labor-saving, time-saving, or the like. Thereby, a large number of diagnoses can be made by a small number of pathologists.

As in the present embodiment, the information based on the image may be input to each of the plurality of learned models, and one piece of information about the diagnosis may be calculated from the information that indicates the diagnosis result output from each of the plurality of learned models. As a result, information that contributes to the objective diagnosis in a reliable and adequate manner can be provided. However, the calculation of the one piece of information about the diagnosis may be performed by a method other than the above method.

As in the present embodiment, in the diagnosis assisting system 1, the machine learning may be performed to generate the learned model. According to this constitution, the individual learned model can be generated, and the present invention can be carried out in an adequate and reliable manner. As in the present embodiment, the generation of the machine learning may be performed in the individual PC 10 rather than the server 20. That is, an architecture of edge heavy computing may be adopted. By adopting the architecture, the diagnosis assisting system 1 can be realized without applying a great load to the server 20. If a user of each PC 10 is a pathologist, the use itself of the diagnosis assisting system 1 by the user also takes charge of data collection, can collect high-quality learning data, and can make the individual learned model high in quality. The individual PC 10 acquires the learning data and performs the machine learning, and thereby the server 20 itself need not acquire the learning data, and can acquire the learned model in a dynamical and efficient way on a large scale.

Results of analyzing the image using the server 20 can also be made to be used from the PCs 10 as in the aforementioned embodiment. That is, the users of the PCs 10 may be made to mutually refer to the information that contributes to the objective diagnosis. According to this constitution, the objective diagnosis can be made in each user, and the diagnostic criterion can be objectified.

However, there is no need to take a constitution in which the generation of the learned model is performed by the individual PC 10, and the generation of the learned model may be performed in the server 20. The diagnosis assisting system 1 may take a constitution in which the learned model is not generated. That is, the diagnosis assisting system 1 may take a constitution without the PCs 10. In this case, the diagnosis assisting system 1 may acquire the plurality of learned models from a system other than the diagnosis assisting system 1.

As in the present embodiment, the learned model may be configured to include the neural network. According to this constitution, the learned model can be made adequate, and the present invention can be carried out in an adequate and reliable manner. However, the learned model may be other than one including the neural network as long as it is generated by the machine learning.

As described above, the diagnosis according to the present embodiment is to determine the presence/absence of the lesion, but it may be a diaganosis other than this diagnosis. For example, the diagnosis may be to determine a state or a numerical value (e.g., an early diagnosis marker value) that indicates the lesion. In the present embodiment, the diagnosis may be intended for animals other than the humans (e.g., domestic animals, pets, laboratory animals) in addition to the humans. In the present embodiment, the diagnosis may be to perform a toxicologic pathological diagnosis.

As described above, in the present embodiment, the diagnosis is intended for the pathological diagnosis, but it may not be necessarily intended for the pathological diagnosis. For example, the image used for the diagnosis may not be the image of the pathological specimen, but an electrocardiogram, an X-ray picture, a computed tomography (CT) image, or a magnetic resonance imaging (MRI) image. The diagnosis may be intended for diagnoses other than the diagnosis related to the lesion.

As described above, in the present embodiment, the information input to the learned model, i.e. the information used for the diagnosis, is the information based on the image, but information other than this information may also be made to be input to the learned model. For example, various blood biochemical parameters of a person subjected to the diagnosis, and an early diagnosis marker value may be made to be input to the learned model.

In the present embodiment, the learned model by the machine learning in which a previous pathological image and a current diagnosis result are used as the learning data may be made to be used. That is, for example, the machine learning may be performed using a previous lesion-free pathological image of a person in which a lesion occurs.

Thereby, with respect to a pathological image (a normal image) from which it can be determined that there is no lesion, it can be determined that a lesion occurs (is abnormalized) later or that a lesion does not occur (is not abnormalized) later. That is, by taking this constitution, an early diagnosis can be made.

The image from which it is determined that there is a lesion may be made to be innumerably generated by backward calculation using the plurality of learned models according to the present embodiment. Thereby, a rare abnormal image that was not known in the past can be discovered.

Continuously, a diagnosis assisting program for causing a computer to execute the above series of processes using the diagnosis assisting system 1 will be described. As illustrated in FIG. 3, a diagnosis assisting program 100 is configured to include a PC-side program 110 and a server-side program 120. The PC-side program 110 is stored in a program storage region 211 which is formed in a recording medium 210 which is inserted into a computer having the same hardware configuration as the above PC 10 and is accessed or which is included in the computer. The server-side program 120 is stored in a program storage region 221 which is formed in a recording medium 220 which is inserted into a computer having the same hardware configuration as the above server 20 and is accessed or which is included in the computer.

The PC-side program 110 is configured to include a learned model generation module 111. A function realized by executing the learned model generation module 111 is the same as that of the learned model generating unit 11 of the above PC 10.

The server-side program 120 is configured to include a learned model acquisition module 121, an image acquisition module 122, a calculation module 123, and an output module 124. Functions realized by executing the learned model acquisition module 121, the image acquisition module 122, the calculation module 123, and the output module 124 are the same as those of the learned model acquisition unit 21, the image acquisition unit 22, the calculation unit 23, and the output unit 24 of the above server 20.

The diagnosis assisting program 100 may be configured such that a part or the whole thereof is transmitted via a transmitting medium such as a communication line, and is received and recorded (including install) by another device. Each module of the diagnosis assisting program 100 may not be installed on one computer, but some of a plurality of computers. In this case, the above series of processes related to the diagnosis assisting program 100 are performed by a computer system including the plurality of computers.

EXPLANATION OF REFERENCE NUMERALS

1 Diagnosis assisting system
10 PC
11 Learned model generating unit
20 Server
21 Learned model acquisition unit
22 Image acquisition unit
23 Calculation unit
24 Output unit
100 Diagnosis assisting program
110 PC-side program
111 Learned model generation module
120 Server-side program
121 Learned model acquisition module
122 Image acquisition module
123 Calculation module
124 Output module
210, 220 Recording medium
211, 221 Program storage region

The invention claimed is:

1. A diagnosis assisting system comprising:
learned model acquisition means configured to acquire a plurality of learned models that are generated by machine learning, input information based on an image obtained by imaging a diagnostic target, and output information that indicates a diagnosis result of the diagnostic target;
image acquisition means configured to acquire an image to be analyzed, wherein the image to be analyzed is an image of a pathological specimen comprising a pathological tissue collected from a body of an animal;
calculation means configured to perform calculation based on the plurality of learned models acquired by the learned model acquisition means on the image acquired by the image acquisition means, and calculate one piece of information about a diagnosis using the plurality of learned models; and
output means configured to output the information calculated by the calculation means, wherein the calculation means inputs information based on the image acquired by the image acquisition means to each of the plurality of learned models acquired by the learned model acquisition means, and calculates information that indicates consistency/inconsistency between the diagnosis result as one piece of information about a diagnosis from information that indicates a diagnosis result output from each of the plurality of learned models.

2. The diagnosis assisting system according to claim 1, further comprising learned model generation means configured to acquire the image obtained by imaging the diagnostic target and the information that indicates the diagnosis result of the diagnostic target, both of which are learning data used for the machine learning, perform the machine learning using information based on the image that is the acquired learning data as an input value and using the information that indicates the diagnosis result and is the acquired learning data as an output value, and generate a learned model,
wherein the learned model acquisition means acquires the learned model generated by the learned model generation means.

3. The diagnosis assisting system according to claim 2, wherein the learned model acquisition means acquires the plurality of learned models including a neural network.

4. The diagnosis assisting system according to claim 1, wherein the learned model acquisition means acquires the plurality of learned models including a neural network.

5. The diagnosis assisting system according to claim 4, wherein the diagnostic target is a plurality of types of lesions, and the output layer of the neural network is provided with a plurality of neurons corresponding to the plurality of types of lesions, and an output value of the neuron is a value corresponding to the diagnostic information of the learning data.

6. The diagnosis assisting system according to claim 1, further comprising learned model generation means configured to acquire the image obtained by imaging the diagnostic target and the information that indicates the diagnosis result of the diagnostic target, both of which are learning data used for the machine learning, perform the machine learning using information based on the image that is the acquired learning data as an input value and using the information that indicates the diagnosis result and is the acquired learning data as an output value, and generate a learned model, wherein the learned model acquisition means acquires the learned model generated by the learned model generation means.

7. The diagnosis assisting system according to claim 1, wherein the learned model acquisition means acquires the plurality of learned models including a neural network.

8. The diagnosis assisting system according to claim 1, wherein the animal is a human.

9. A diagnosis assisting method that is a method for operating a diagnosis assisting system comprising:

a learned model acquiring step of acquiring a plurality of learned models that are generated by machine learning, input information based on an image obtained by imaging a diagnostic target, and output information that indicates a diagnosis result of the diagnostic target;

an image acquiring step of acquiring an image to be analyzed, wherein the image to be analyzed is an image of a pathological specimen comprising a pathological tissue collected from a body of an animal;

a calculating step of performing calculation based on the plurality of learned models acquired in the learned model acquisition step on the image acquired in the image acquisition step, and calculating one piece of information about a diagnosis using the plurality of learned models; and an outputting step of outputting the information calculated in the calculating step, wherein the calculation means inputs information based on the image acquired by the image acquisition means to each of the plurality of learned models acquired by the learned model acquisition means, and calculates information that indicates consistency/inconsistency between the diagnosis result as one piece of information about a diagnosis from information that indicates a diagnosis result output from each of the plurality of learned models.

10. The diagnosis assisting method according to claim 9, wherein the animal is a human.

\* \* \* \* \*